(12) United States Patent
Seifert

(10) Patent No.: US 11,867,943 B2
(45) Date of Patent: Jan. 9, 2024

(54) OPTICAL FIBERS, METHODS OF THEIR FORMATION, AND METHODS OF THEIR USE

(71) Applicant: SpectraWAVE, Inc., Bedford, MA (US)

(72) Inventor: Martin F. Seifert, New Hartford, CT (US)

(73) Assignee: Spectra WAVE, Inc., Bedford, MA (US)

( * ) Notice: Subject to any disclaimer, the term of this patent is extended or adjusted under 35 U.S.C. 154(b) by 53 days.

(21) Appl. No.: 17/291,921

(22) PCT Filed: Nov. 6, 2019

(86) PCT No.: PCT/US2019/060158
§ 371 (c)(1),
(2) Date: May 6, 2021

(87) PCT Pub. No.: WO2020/097267
PCT Pub. Date: May 14, 2020

(65) Prior Publication Data
US 2022/0011506 A1    Jan. 13, 2022

Related U.S. Application Data
(60) Provisional application No. 62/757,152, filed on Nov. 7, 2018.

(51) Int. Cl.
*G02B 6/36*        (2006.01)
*G02B 6/036*       (2006.01)
(Continued)

(52) U.S. Cl.
CPC ...... *G02B 6/03694* (2013.01); *C03B 37/0122* (2013.01); *G02B 6/02342* (2013.01); *G02B 6/03627* (2013.01); *C03B 2201/30* (2013.01)

(58) Field of Classification Search
CPC . G02B 6/03633; G02B 6/03694; G02B 6/266
See application file for complete search history.

(56) References Cited

U.S. PATENT DOCUMENTS

| | | | |
|---|---|---|---|
| 6,625,364 B2 * | 9/2003 | Johnson ............ | G02B 6/02304 385/127 |
| 7,526,167 B1 * | 4/2009 | Minelly ............ | G02B 6/03633 359/341.3 |

(Continued)

FOREIGN PATENT DOCUMENTS

| CN | 111202500 A | * | 5/2020 | ........... A61B 5/0066 |
|---|---|---|---|---|
| JP | 2004 333909 A | | 11/2004 | |

(Continued)

OTHER PUBLICATIONS

Belanov, A. et al., On the possibility of compensating material dispersion in three-layer optical fibres in the wavelength range below 1.3 μm, Quantum Electronics, 32(5):425-427 (2002).

(Continued)

*Primary Examiner* — Eric Wong
(74) *Attorney, Agent, or Firm* — Choate, Hall & Stewart LLP; Brenda Herschbach Jarrell; Michael D. Schmitt

(57) ABSTRACT

An example of an optical fiber includes an attenuating cladding disposed around a first waveguide (e.g., a core) and a waveguide (e.g., a waveguide cladding) disposed around the attenuating cladding. An attenuating cladding may be a doped layer that may be doped with, for example, a dopant comprising metal. A first waveguide and a second waveguide may each transmit light for a distinct sample characterization technique. An example of an optical fiber includes a core, a first intermediate cladding disposed around the core, an attenuating cladding disposed around the first intermediate cladding, an attenuating cladding disposed around the first intermediate cladding, a second intermediate cladding disposed around the attenuating cladding, a wave- (Continued)

guide cladding disposed around the second intermediate cladding, and outer cladding disposed around the waveguide cladding, and an outer coating around the outer cladding. An optical fiber may be formed using a rod-in-tube process.

27 Claims, 5 Drawing Sheets

(51) Int. Cl.
    *C03B 37/012*     (2006.01)
    *G02B 6/02*     (2006.01)

(56) References Cited

U.S. PATENT DOCUMENTS

| | | | |
|---|---|---|---|
| 7,835,608 B2 | 11/2010 | Minelly et al. | |
| 2002/0126971 A1 | 9/2002 | Soufiane | |
| 2011/0176783 A1* | 7/2011 | Ooizumi | C03B 37/01446 385/127 |
| 2014/0199039 A1* | 7/2014 | Kokubun | G02B 6/46 29/428 |
| 2018/0259317 A1 | 9/2018 | Tearney et al. | |
| 2019/0072713 A1* | 3/2019 | Yoo | G02B 6/266 |
| 2019/0150720 A1* | 5/2019 | Altshuler | A61B 5/7203 |

FOREIGN PATENT DOCUMENTS

| | | | |
|---|---|---|---|
| KR | 20170102091 A | 9/2017 | |
| WO | WO-2010035397 A1 * | 4/2010 | ....... C03B 37/01446 |
| WO | WO-2020/097267 A1 | 5/2020 | |

OTHER PUBLICATIONS

International Search Report for PCT/US2019/060158 (Optical Fibers, Methods of Their Formation, and Methods of Their Use, filed Nov. 6, 2019) received from ISA/EP, 6 pages (dated Mar. 27, 2020).
Lombardini, A. et al., Nonlinear endoscopy with Kagome lattice hollow-core fibers (Conference Presentation), Progress in Biomedical Optics and Imaging Spie—International Society for Optical Engineering, 9691:969101-969101 (2016).
Lu, Y. et al., Catheter-based time-gated near-infrared fluorescence/ OCT imaging system, Progress in Biomedical Optics and Imaging Spie—International Society for Optical Engineering, 10471: 8 pages (2018).
Stawska H. et al., Numerical Estimation of Ultrafast Pulse Propagation in Double Clad Hollow Core Fibers, 2013 15th International conference on Transparent Optical Networks, IEEE, pp. 1-5 (2013).
Stawska, H. and Beres-Pawlik, E., Enhancement of two photon fluorescence collection by using effectively single mode double clad hollow core fiber with low dispersion at 800 nm, Opt Quant Electron, 47:67-76 (2015).
Written Opinion for PCT/US2019/060158 (Optical Fibers, Methods of Their Formation, and Methods of Their Use, filed Nov. 6, 2019) received from ISA/EP, 12 pages (dated Mar. 27, 2020).

* cited by examiner

OPTICAL FIBERS, METHODS OF THEIR FORMATION, AND METHODS OF THEIR USE

PRIORITY APPLICATIONS

This application is a national stage entry under 35 U.S.C. § 371 of International (PCT) Application No. PCT/US19/60158, filed on Nov. 6, 2019, which claims the benefit of U.S. Provisional Patent Application No. 62/757,152, filed on Nov. 7, 2018, the disclosure of which is hereby incorporated by reference herein in its entirety.

BACKGROUND

Optical fibers are used to transmit signals using light. One or more modes of light can travel through a given optical fiber. Some fibers comprise multiple layers including a core and a cladding that are each engineered to transmit at least one distinct mode of light. Examples of such fibers include multi-clad fibers (e.g., double clad fibers). Multi-clad fibers are typically made of layers of glass and/or plastic around each other. Multi-clad fibers may be used in applications with multiple signals being transmitted in place of a plurality of separate fibers (i.e., optically separate fibers, each having its own core).

SUMMARY

Multi-clad fibers can be used to carry multiple independent signals. Even when signal launch, splice, and/or connector conditions are optimized, some amount of signal mixing and/or perturbation of the independent signals exists. For example, a cladding can communicate with a core, for example, through minor cladding shape perturbations. As another example, a core can communicate with a cladding, for example, through bending. If independent signals are desirable then communication between different layers that are intended to independently transmit signals (e.g., a core and a cladding in certain multi-clad fibers) is undesirable. The present disclosure recognizes that such communication is particularly undesirable when the fiber is used with a fiber optic rotary junction (e.g., in a catheter). For example, such communication is undesirable when a fiber is a multi-clad fiber used to transmit and receive signals, for example, for optical coherence tomography.

Light may be leaked (e.g., lost) from a waveguide in a fiber having one or more waveguides (e.g., a core and/or a waveguide cladding). Light leaked (e.g., lost) from a first waveguide may propagate along a second waveguide before reentering the first waveguide with a phase shift (due to propagation path length difference), for example. In a simple example, a fiber has a core, a single cladding, and a coating, and most or all of the leaked (e.g., lost) light is absorbed by the opaque coating before it can reenter the core. A similar effect occurs in multimode fibers. The present disclosure recognizes that the lost light extinction benefit obtained by the coating in a simple fiber is not inherently present for all waveguides in a conventional multi-clad fiber. There is a problem in that light which leaks into a cladding can further propagate into adjacent claddings and, moreover, is free to re-enter a core or inner cladding at a spatially separated location. Such a path length difference can cause signal interference (e.g., dispersion), cancellation, or attenuation (e.g., destructive interference). A solution disclosed herein is to use to an attenuating cladding disposed between waveguides in an optical fiber. In some embodiments, an attenuating cladding strongly attenuates light and, therefore, may entirely optically isolate two waveguides (e.g., a core and concentric cladding).

Apparatus disclosed herein include optical fibers (e.g., characterization fibers) comprising an attenuating cladding disposed between two waveguides (e.g., a core and a waveguide cladding). An attenuating cladding may improve confinement of light transmitted through a waveguide of a fiber. In some embodiments, an optical fiber is a characterization fiber comprising at least two waveguides, each constructed, sized, and shaped to transmit light (e.g., illumination light and/or sample signal light) for a sample characterization technique (e.g., imaging or spectroscopy). Improved confinement between waveguides in a fiber reduces deleterious effects on transmitted signals that may, for example, reduce image quality of images generated using the signals.

In some aspects, this disclosure provides an optical fiber comprising a first waveguide, an attenuating cladding disposed around the first waveguide, and a second waveguide disposed around the attenuating cladding. A first waveguide may be a core. A second waveguide may be a waveguide cladding. An optical fiber may be a characterization fiber used for transmitting and/or receiving signals for a sample characterization technique.

In some embodiments, an attenuating cladding comprises a dopant. In some embodiments, an attenuating cladding comprises a glass and a dopant dispersed within the glass. In some embodiments, a dopant comprises a metal. In some embodiments, a dopant comprises a metallic oxide or a metallic chloride. In some embodiments, a dopant is a pure metal. In some embodiments, a dopant comprises boron. In some embodiments, a dopant may comprise one or more Rayleigh scatterers. In some embodiments, an attenuating cladding is opaque.

In some embodiments, an attenuation length of an attenuating cladding is no more than 1 meter (e.g., no more than 30 mm) (e.g., at a wavelength corresponding to a second waveguide or a wavelength corresponding to a first waveguide, or both a wavelength corresponding to a second waveguide and a wavelength corresponding to a first waveguide). In some embodiments, an attenuating cladding has an attenuation length of between 5 mm and 35 mm (e.g., between 10 mm and 30 mm, between 12 mm and 28 mm, between 15 mm and 25 mm, between 17 mm and 23 mm, or between 19 mm and 21 mm). In some embodiments, an attenuating cladding has an attenuation length of about 20 mm. In some embodiments, an attenuating cladding is constructed, sized, and shaped to attenuate at least 90% (e.g., at least 95%, at least 97%, or at least 99%) of light in a distance of at least 3 mm (e.g., at least 5 mm, at least 8 mm, at least 10 mm, at least 15 mm, or at least 20 mm) and no more than 1 m (e.g., no more than 500 mm, no more than 300 mm, no more than 250 mm, no more than 200 mm, no more than 100 mm, no more than 50 mm, no more than 30 mm, or no more than 20 mm). In some embodiments, an attenuating cladding is constructed, sized, and shaped to attenuate at least 90% (e.g., at least 95%, at least 97%, or at least 99%) of light in a distance of between 5 mm and 35 mm (e.g., between 10 mm and 30 mm, between 12 mm and 28 mm, between 15 mm and 25 mm, between 17 mm and 23 mm, or between 19 mm and 21 mm). In some embodiments, an attenuating cladding is constructed, sized, and shaped to attenuate at least 90% (e.g., at least 95%, at least 97%, or at least 99%) of light in a distance of about 20 mm. In some embodiments, an imaginary part of a refractive index of an attenuating cladding is higher than an imaginary part of a refractive index of the first waveguide and an imaginary part of a refractive index of a second waveguide.

In some aspects, the present disclosure provides a system comprising an optical fiber, a rotary junction, and a probe, wherein the optical fiber is in optical communication with the rotary junction (e.g., wherein the optical fiber is physically connected to the rotary junction) and the probe is in optical communication with the rotary junction (e.g., and wherein the probe is physically connected to the rotary junction).

In some aspects, the present disclosure provides a catheter (e.g., a cardiac catheter) comprising an optical fiber, a first light source, and a second light source, wherein the first light source is in optical communication with a first waveguide of the optical fiber and the second light source is in optical communication with a second waveguide of the optical fiber. In some embodiments, a system comprises an imaging module (e.g., for OCT imaging) and a spectroscopy module (e.g., for near-infrared spectroscopy), wherein the imaging module comprises one of a first light source and a second light source and the spectroscopy module comprises a different one of the first light source and the second light source.

In some aspects, the present disclosure provides a method comprising disposing a first tube comprising attenuating-cladding material around a rod comprising solid-core material; disposing a second tube comprising waveguide-cladding material around the first tube; simultaneously heating the first tube, the second tube, and the rod to make a fused preform; and drawing the fused preform in order to form an optical fiber (e.g., and optionally coating the drawn fused preform with an outer coating).

In some aspects, the present disclosure provides a method comprising disposing an attenuating tube comprising attenuating-cladding material around a first tube comprising first waveguide material; disposing a second tube comprising second waveguide material around the attenuating tube; simultaneously heating the first tube, the second tube, and the attenuating tube to make a fused preform; and drawing the fused preform in order to form an optical fiber (e.g., and optionally coating the drawn fused preform with an outer coating).

In some aspects, the present disclosure provides a method of using an optical fiber comprising: providing an optical fiber comprising a first waveguide (e.g., a core), an attenuating cladding disposed around the first waveguide, and a second waveguide (e.g., a waveguide cladding) disposed around the attenuating cladding; transmitting a first signal through the first waveguide; and transmitting a second signal through the second waveguide.

In some embodiments, a first signal and a second signal are transmitted during a same period of time. In some embodiments, a method of using an optical fiber comprises completely attenuating a first portion of a first signal with an attenuating cladding (e.g., wherein the first portion propagates (e.g., leaks) from a first waveguide into the attenuating cladding and is completely attenuated by the attenuating cladding (e.g., such that the first portion cannot propagate from the attenuating cladding (e.g., into a waveguide cladding or core)) (e.g., due to absorption of the first portion)).

BRIEF DESCRIPTION OF THE DRAWING

The drawing is presented herein for illustration purposes, not for limitation. The foregoing and other objects, aspects, features, and advantages of various embodiments will become more apparent and may be better understood by referring to the following description taken in conjunction with the accompanying drawing, in which.

Figure 2:
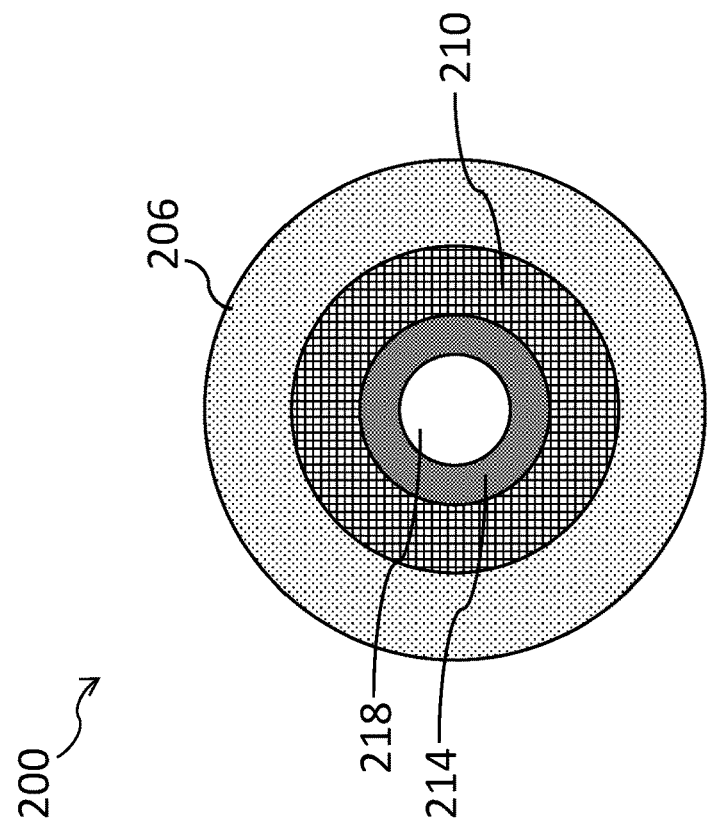
FIG. 2 shows a cross-section of an example of an optical fiber with an attenuating cladding and two waveguide claddings, according to illustrative embodiments of the disclosure.

Figures are not necessarily drawn to scale.

DETAILED DESCRIPTION OF CERTAIN EMBODIMENTS

Throughout the description, where articles, devices, and systems are described as having, including, or comprising specific components, or where processes and methods are described as having, including, or comprising specific steps, it is contemplated that, additionally, there are articles, devices, and systems of the present disclosure that consist essentially of, or consist of, the recited components, and that there are processes and methods according to the present disclosure that consist essentially of, or consist of, the recited processing steps. Where a component is described as being "arranged and constructed to" provide or perform (e.g., a function or step of a method), embodiments are contemplated where that component is programmed or otherwise settable to provide or perform (e.g., the function or step of the method). For example, a light source arranged and constructed to have a bright phase may be programmed to have a bright phase or may be set (e.g., using one or more physical controls) to have a bright phase.

It should be understood that the order of steps or order for performing certain action is immaterial so long as the method to which the steps or actions belong remains operable. Moreover, in some embodiments, two or more steps or actions may be conducted simultaneously.

In this application, unless otherwise clear from context or otherwise explicitly stated, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) the terms "about" and "approximately" may be understood to permit standard variation as would be understood by those of ordinary skill in the art; and (v) where ranges are provided, endpoints are included. As used herein, "first" and "second" are arbitrary designations and are not meant to be limiting. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

In some embodiments, an optical fiber comprises an attenuating cladding. An optical fiber may comprise a first waveguide (e.g., a solid core, a hollow core, or a waveguide cladding), a second waveguide (e.g., a waveguide cladding), and an attenuating cladding (e.g., disposed between the first waveguide and the second waveguide). In some embodiments, an attenuating cladding is disposed around a first waveguide. In some embodiments, a second waveguide is disposed around an attenuating cladding. An attenuating cladding attenuates light of at least one wavelength. An attenuating cladding may comprise a polymer and/or a glass. In some embodiments, an attenuating cladding comprises a glass. A waveguide (e.g., a core or a waveguide cladding) may comprise a polymer and/or a glass. In some embodiments, a waveguide comprises a glass. In some embodiments, an optical fiber comprises an attenuating cladding between each pair of adjacent waveguides. For example, an optical fiber may comprise three waveguides (e.g., a core, a first waveguide cladding, and a second waveguide cladding) and two attenuating claddings in a spatial sequence of: waveguide, attenuating cladding, waveguide, attenuating cladding, and waveguide.

In some embodiments, a waveguide (e.g., a waveguide cladding or a core) is constructed, sized, and shaped to substantially confine light of a wavelength or a range of wavelengths (e.g., corresponding to a characterization technique). In some embodiments, a first waveguide (e.g., a core or waveguide cladding) is constructed, sized, and shaped to substantially confine light of a first wavelength or a range of first wavelengths and a second waveguide (e.g., a waveguide cladding) is constructed, sized, and shaped to substantially confine light of a second wavelength or a range of second wavelengths. For example, a waveguide cladding may transmit a signal using light of a first wavelength or a range of first wavelengths independently of a core transmitting a signal using light of a second wavelength or a range of second wavelengths. A first wavelength or range of first wavelengths may be the same, different, or partially overlap a second wavelength or range of second wavelengths. In some embodiments, an attenuating cladding may limit or prevent light from a first waveguide from entering (e.g., propagating or interfering with) a second waveguide.

A waveguide cladding may be a single-mode or multi-mode waveguide. A waveguide cladding may be a single-mode or multi-mode waveguide. A core may be a single-mode or multi-mode waveguide. A waveguide may be constructed, sized, and shaped to transmit light of one or more wavelengths. A core may be constructed, sized, and shaped to transmit light of one or more wavelengths. A waveguide cladding may be constructed, sized, and shaped to transmit light of one or more wavelengths. A waveguide (e.g., a core or waveguide cladding) may be constructed, sized, and shaped to transmit light of one or more wavelengths to transmit a single wavelength or a narrow or wide band of wavelengths. For example, a band of wavelengths may be no more than 500 nm wide, no more than 400 nm wide, no more than 300 nm wide, no more than 200 nm wide, no more than 100 nm wide, no more than 75 nm wide, no more than 50 nm wide, no more than 30 nm wide, no more than 20 nm wide, or no more than 10 nm wide. A waveguide (e.g., a core or waveguide cladding) may be constructed, sized, and shaped to transmit light of one or more wavelengths used in a sample characterization technique. A waveguide (e.g., a core or waveguide cladding) may be constructed, sized, and shaped to transmit light received from a light source, such as a light-emitting diode, a superluminescent diode, or a laser.

An optical fiber may comprise one or more waveguides that are used to transmit light (e.g., illumination light or light from a sample) for one or more sample characterization techniques. For example, an optical fiber may comprise two waveguides (e.g., a core and a waveguide cladding) and transmit light for a distinct technique separately through each of the two waveguides. A waveguide of an optical fiber may be constructed, sized, and shaped to transmit light for an imaging technique (e.g., a tomography technique) or a spectroscopy technique. A waveguide of an optical fiber may be constructed, sized, and shaped to transmit light, for example, for UV-vis spectroscopy, infrared spectroscopy (e.g., near-infrared spectroscopy (NIRS)), or photoluminescence spectroscopy. In some embodiments, a waveguide of an optical fiber may be constructed, sized, and shaped to transmit light for near-infrared spectroscopy. A waveguide of an optical fiber may be constructed, sized, and shaped to transmit light for a 2D imaging technique or a 3D imaging technique (e.g., a tomography technique). A waveguide of an optical fiber may be constructed, sized, and shaped to transmit light, for example, for an optical imaging technique. An optical imaging technique may be, for example, fluorescence imaging, such as fluorescence tomography. An optical imaging technique may be, for example, optical coherence tomography (OCT) or diffuse optical imaging (e.g., diffuse optical tomography). A waveguide of an optical fiber may be constructed, sized, and shaped to transmit light, for example, for an interferometry technique (e.g., OCT). A waveguide of an optical fiber may be constructed, sized, and shaped to transmit light, for example, for a phase imaging technique. A waveguide of an optical fiber may be constructed, sized, and shaped to transmit light for a characterization technique where a wavelength (e.g., central wavelength in a range) of the light corresponds to a characterization peak for a sample. For example, a characterization peak may correspond to a material in a vulnerable plaque (e.g., cholesterol) (e.g., when an optical fiber is used in a cardiac catheter).

An attenuating cladding may comprise a dopant. An attenuating cladding may comprise a polymer and/or a glass. In some embodiments, an attenuating cladding comprises a dopant dispersed in a glass. An attenuating cladding may comprise a dopant dispersed in polymer. In some embodiments, an attenuating cladding comprises a dopant comprising a metal. In some embodiments, for example, an attenuating cladding comprises a dopant comprising cobalt. In some embodiments, a dopant may be a metallic oxide or a metallic chloride. In some embodiments, a dopant is a pure metal. In some embodiments, a dopant comprises boron. In some embodiments, a dopant comprises carbon. In some embodiments, a dopant comprises ytterbium (e.g., when used in a fiber constructed, sized, and shaped to transmit light at a non-pumped wavelength). In some embodiments, a dopant may comprise one or more Rayleigh scatterers (e.g., particles). In some embodiments, an attenuating cladding is opaque (e.g., is a well-defined opaque layer between two waveguides (e.g., concentric waveguides) in a fiber).

In some embodiments, an attenuating cladding has an attenuation length that is no more than 1 meter (e.g., no more than 500 mm, no more than 300 mm, no more than 250 mm, no more than 200 mm, no more than 100 mm, no more than 50 mm, no more than 30 mm, no more than 20 mm, no more than 15 mm, no more than 10 mm, no more than 7 mm, no more than 5 mm, no more than 3 mm, no more than 1 mm, no more than 0.5 mm, or no more than 0.1 mm). An attenuating cladding with a very long attenuation length (e.g., appreciably exceeding 1 meter) may allow light to undesirably re-enter a waveguide from the attenuating cladding (e.g., with a phase shift). In some embodiments, an attenuating cladding has an attenuation length that is no more than 1 meter (e.g., no more than 500 mm, no more than 300 mm, no more than 250 mm, no more than 200 mm, no more than 100 mm, no more than 50 mm, no more than 30 mm, no more than 20 mm, no more than 15 mm, no more than 10 mm, no more than 7 mm, no more than 5 mm, no more than 3 mm, no more than 1 mm, no more than 0.5 mm, or no more than 0.1 mm) at a wavelength corresponding to a waveguide of an optical fiber. In some embodiments, an attenuating cladding has an attenuation length that is no more than 1 meter (e.g., no more than 500 mm, no more than 300 mm, no more than 250 mm, no more than 200 mm, no more than 100 mm, no more than 50 mm, no more than 30 mm, no more than 20 mm, no more than 15 mm, no more than 10 mm, no more than 7 mm, no more than 5 mm, no more than 3 mm, no more than 1 mm, no more than 0.5 mm, or no more than 0.1 mm) at a wavelength corresponding to a first waveguide (e.g., a waveguide cladding or a core), a wavelength corresponding to a second waveguide (e.g., a waveguide cladding or a core), or both a wavelength corresponding to first waveguide and a wavelength corresponding to a second waveguide (e.g., wherein the first waveguide is a core and the second waveguide is a waveguide cladding). In some embodiments, an attenuating cladding with a short attenuation length may assist in attenuating (e.g., completely) light leaked from a first waveguide (e.g., a core or a waveguide cladding) so that it cannot enter (e.g., interfere with or propagate along) a second waveguide disposed on a side of the attenuating cladding opposite the first waveguide.

In some embodiments, an attenuating cladding has an attenuation length that is at least 3 mm (e.g., at least 5 mm, at least 8 mm, at least 10 mm, at least 15 mm, or at least 20 mm) and no more than 1 m (e.g., no more than 500 mm, no more than 300 mm, no more than 250 mm, no more than 200 mm, no more than 100 mm, no more than 50 mm, no more than 30 mm, or no more than 20 mm). In some embodiments, an attenuating cladding has an attenuation length that is between 5 mm and 35 mm (e.g., between 10 mm and 30 mm, between 12 mm and 28 mm, between 15 mm and 25 mm, between 17 mm and 23 mm, or between 19 mm and 21 mm). In some embodiments, an attenuating cladding has an attenuation length that is about 20 mm. In some embodiments, an attenuating cladding has an attenuation length that is about 15 mm. In some embodiments, an attenuating cladding has an attenuation length that is about 10 mm. In some embodiments, an optical fiber comprising an attenuating cladding having an intermediate attenuation length (e.g., at least 3 mm and no more than 1 m or between 5 mm and 35 mm) produces small thermal gradients formed in the optical fiber due to attenuation in the attenuating cladding (e.g., as compared to an attenuating cladding having a shorter attenuation length, which may concentrate heat caused by attenuation). Without wishing to be bound to any particular theory, large thermal gradients may cause back reflections that may be detrimental to light transmission through a waveguide.

In some embodiments, an attenuating cladding attenuates (e.g., is constructed, sized, and shaped to attenuate) at least 90% (e.g., at least 95%, at least 97%, or at least 99%) of light in a distance of no more than 1 meter (e.g., no more than 500 mm, no more than 300 mm, no more than 250 mm, no more than 200 mm, no more than 100 mm, no more than 50 mm, no more than 30 mm, no more than 20 mm, no more than 15 mm, no more than 10 mm, no more than 7 mm, no more than 5 mm, no more than 3 mm, no more than 1 mm, no more than 0.5 mm, or no more than 0.1 mm). In some embodiments, an attenuating cladding attenuates (e.g., is constructed, sized, and shaped to attenuate) at least 90% (e.g., at least 95%, at least 97%, or at least 99%) of light in a distance of no more than 1 meter (e.g., no more than 500 mm, no more than 300 mm, no more than 250 mm, no more than 200 mm, no more than 100 mm, no more than 50 mm, no more than 30 mm, no more than 20 mm, no more than 15 mm, no more than 10 mm, no more than 7 mm, no more than 5 mm, no more than 3 mm, no more than 1 mm, no more than 0.5 mm, or no more than 0.1 mm) at a wavelength corresponding to a first waveguide (e.g., a waveguide cladding or a core), a wavelength corresponding to a second waveguide (e.g., a waveguide cladding or a core), or both a wavelength corresponding to first waveguide and a wavelength corresponding to a second waveguide (e.g., wherein the first waveguide is a core and the second waveguide is a waveguide cladding).

In some embodiments, an attenuating cladding attenuates (e.g., is constructed, sized, and shaped to attenuate) at least 90% (e.g., at least 95%, at least 97%, or at least 99%) of light in a distance of at least 3 mm (e.g., at least 5 mm, at least 8 mm, at least 10 mm, at least 15 mm, or at least 20 mm) and no more than 1 m (e.g., no more than 500 mm, no more than 300 mm, no more than 250 mm, no more than 200 mm, no more than 100 mm, no more than 50 mm, no more than 30 mm, or no more than 20 mm). In some embodiments, an attenuating cladding attenuates (e.g., is constructed, sized, and shaped to attenuate) at least 90% (e.g., at least 95%, at least 97%, or at least 99%) of light in a distance of between 5 mm and 35 mm (e.g., between 10 mm and 30 mm, between 12 mm and 28 mm, between 15 mm and 25 mm, between 17 mm and 23 mm, or between 19 mm and 21 mm). In some embodiments, an attenuating cladding attenuates (e.g., is constructed, sized, and shaped to attenuate) at least 90% (e.g., at least 95%, at least 97%, or at least 99%) of light in a distance of about 20 mm. In some embodiments, an attenuating cladding attenuates (e.g., is constructed, sized, and shaped to attenuate) at least 90% (e.g., at least 95%, at least 97%, or at least 99%) of light in a distance of about 15 mm. In some embodiments, an attenuating cladding attenuates (e.g., is constructed, sized, and shaped to attenuate) at least 90% (e.g., at least 95%, at least 97%, or at least 99%) of light in a distance of about 10 mm. In some embodiments, an optical fiber comprising an attenuating cladding that attenuates (e.g., is constructed, sized, and shaped to attenuate) at least 90% of light in a distance of intermediate length (e.g., at least 3 mm and no more than 1 m or between 5 mm and 35 mm) produces small thermal gradients formed in the optical fiber due to attenuation in the attenuating cladding (e.g., as compared to an attenuating cladding that attenuates at least 90% within a shorter distance, which may concentrate heat caused by attenuation). Without wishing to be bound to any particular theory, large thermal gradients may cause back reflections that may be detrimental to light transmission through a waveguide.

A wavelength corresponding to a waveguide of an optical fiber may be a wavelength (e.g., a central wavelength of a narrow or wide band) used in a characterization technique. A wavelength corresponding to a waveguide may be a wavelength for an imaging technique (e.g., a tomography technique) or a spectroscopy technique. A wavelength corresponding to a waveguide may be a wavelength, for example, for UV-vis spectroscopy, infrared spectroscopy (e.g., near-infrared spectroscopy (NIRS)), or photoluminescence spectroscopy. In some embodiments, a wavelength corresponding to a waveguide may be a wavelength for near-infrared spectroscopy. A wavelength corresponding to a waveguide may be a wavelength for a 2D imaging technique or a 3D imaging technique (e.g., a tomography technique). A wavelength corresponding to a waveguide may be a wavelength for an optical imaging technique. An optical imaging technique may be, for example, fluorescence imaging, such as fluorescence tomography. An optical imaging technique may be, for example, optical coherence tomography (OCT) or diffuse optical imaging (e.g., diffuse optical tomography). A wavelength corresponding to a waveguide may be a wavelength for an interferometry technique (e.g., OCT). A wavelength corresponding to a waveguide may be a wavelength for a phase imaging technique. A wavelength corresponding to a waveguide may be a wavelength (e.g., central wavelength in a range) that corresponds to a characterization peak for a sample. For example, a characterization peak may correspond to a material in a vulnerable plaque (e.g., cholesterol) (e.g., when an optical fiber is used in a cardiac catheter).

In some embodiments, an attenuating cladding has an attenuation length that is no more than 80% (e.g., no more than 60%, no more than 50%, no more than 40%, no more than 33%, no more than 20%, no more than 15%, no more than 10%, no more than 7%, no more than 5%, no more than 2%, no more than 1%, no more than 0.5%, no more than 0.1%, or no more than 0.01%) of an attenuation length of at least one adjacent cladding (e.g., a first intermediate cladding, a second intermediate cladding, or both a first intermediate cladding and a second intermediate cladding). In some embodiments, an attenuating cladding in an optical fiber has an attenuation length that is no more than 80% (e.g., no more than 60%, no more than 50%, no more than 40%, no more than 33%, no more than 20%, no more than 10%, no more than 5%, no more than 3%, no more than 2%, no more than 1%, no more than 0.5% no more than 0.3%, no more than 0.2%, no more than 0.1%, or no more than 0.05%) of an attenuation length of at least one waveguide in the optical fiber (e.g., a waveguide cladding, a core, or a waveguide cladding and a core).

In some embodiments, an imaginary part of a refractive index (extinction coefficient) of an attenuating cladding is higher than an imaginary part of a refractive index of a first waveguide, an imaginary part of a refractive index of a second waveguide, or both an imaginary part of a refractive index of a first waveguide and an imaginary part of a refractive index of a second waveguide. In some embodiments, an imaginary part of a refractive index of an attenuating cladding is higher than an imaginary part of a refractive index of a core, an imaginary part of a refractive index of a waveguide cladding, or both an imaginary part of a refractive index of a core and an imaginary part of a refractive index of a waveguide cladding. In some embodiments, an imaginary part of a refractive index (extinction coefficient) of an attenuating cladding is higher than an imaginary part of a refractive index of at least one adjacent cladding (e.g., a first intermediate cladding, a second intermediate cladding, or both a first intermediate cladding and a second intermediate cladding).

In some embodiments, an optical fiber comprises a core (e.g., a solid core or a hollow core). In some embodiments, an optical fiber comprises an attenuating cladding. In some embodiments, an optical fiber comprises a waveguide cladding. In some embodiments, an optical fiber comprises an attenuating cladding disposed around (e.g., surrounding at least one exterior surface of) a first waveguide (e.g., a core or a waveguide cladding). In some embodiments, an optical fiber comprises a waveguide cladding disposed around (e.g., surrounding at least one exterior surface of) an attenuating cladding. In some embodiments, an optical fiber comprises a core, an attenuating cladding disposed around the core, and a waveguide cladding disposed around the attenuating cladding. An attenuating cladding may be disposed around a core. A waveguide cladding may be disposed around an attenuating cladding. A waveguide cladding may be disposed around an attenuating cladding, which is disposed around a core. In some embodiments, a first layer (e.g., a waveguide cladding, an intermediate cladding, or an attenuating cladding) is disposed around (e.g., surrounding at least one exterior surface of) a second layer (e.g., a waveguide cladding, an intermediate cladding, an attenuating cladding, or a core). A first layer (e.g., a waveguide cladding, an intermediate cladding, or an attenuating cladding) disposed around a second layer (e.g., a waveguide cladding, an intermediate cladding, an attenuating cladding, or a core) may be in direct contact with the second layer or there may be one or more layers (e.g., a waveguide cladding, an intermediate cladding, or an attenuating cladding) disposed therebetween.

In some embodiments, an optical fiber comprises two or more layers (e.g., a waveguide cladding, an intermediate cladding, an attenuating cladding, and/or a core) that are concentric. In some embodiments, an optical fiber comprises two or more layers (e.g., a waveguide cladding, an intermediate cladding, an attenuating cladding, and/or a core) that are not concentric. In some embodiments, an optical fiber comprises two or more layers (e.g., a waveguide cladding, an intermediate cladding, an attenuating cladding, and/or a core) that are concentric and one or more layers (e.g., a waveguide cladding, an intermediate cladding, an attenuating cladding, and/or a core) that are not concentric. In some embodiments, one or more layers (e.g., a waveguide cladding, an intermediate cladding, an attenuating cladding, and/or a core) each have an outer surface that is circular in cross section (e.g., are cylindrical or ring-shaped).

In some embodiments, an optical fiber comprises one or more intermediate claddings. An intermediate cladding may be disposed between two waveguides (e.g., a core and a waveguide cladding or a first waveguide cladding and a second waveguide cladding) (e.g., disposed around one of the waveguides). In some embodiments, an attenuating cladding is disposed between (e.g., adjacent to) two intermediate claddings. In some embodiments, an attenuating cladding is in contact with two intermediate claddings (e.g., one in contact with an outer surface of the attenuating cladding and one in contact with an inner surface of the attenuating cladding). An attenuating cladding may be disposed around a first intermediate cladding. A second intermediate cladding may be disposed around an attenuating cladding. An attenuating cladding may be disposed between a first intermediate cladding and a second intermediate cladding. In some embodiments, two intermediate claddings have the same thickness. In some embodiments, two intermediate claddings have different thicknesses. In some embodiments, two intermediate claddings comprise a common material. In some embodiments, two intermediate claddings comprise no common materials. In some embodiments, two intermediate claddings have the same refractive indices. In some embodiments, two intermediate claddings have different refractive indices.

An intermediate cladding may be in direct contact with a waveguide (e.g., a core or a waveguide cladding). For example, a first intermediate cladding may be in direct contact with a first waveguide (e.g., a core) and/or a second intermediate cladding may be in direct contact with a second waveguide (e.g., a waveguide cladding). In some embodiments, an intermediate cladding has a lower refractive index than a waveguide (e.g., that it is in direct contact with). An intermediate cladding may comprise a polymer and/or a glass.

In some embodiments, an optical fiber comprises an outer cladding that is disposed around a waveguide (e.g., a waveguide cladding that may be an outermost waveguide). An outer cladding may be in direct contact with a waveguide (e.g., a waveguide cladding that may be an outermost waveguide). In some embodiments, an outer cladding has a lower refractive index than a waveguide (e.g., that it is in direct contact with). In some embodiments, an outer cladding and an intermediate cladding have the same thickness. In some embodiments, an outer cladding and an intermediate cladding have different thicknesses. In some embodiments, an outer cladding and an intermediate cladding comprise a common material. In some embodiments, an outer cladding and an intermediate cladding comprise no common materials. In some embodiments, an outer cladding and an intermediate cladding have the same refractive indices. In some embodiments, an outer cladding and an intermediate cladding have different refractive indices.

In some embodiments, an optical fiber comprises an outermost layer. For example, an outermost layer may be disposed around an outer cladding (e.g., such that the outer cladding is disposed between the outer coating and a waveguide (e.g., a waveguide cladding, such as an outermost waveguide cladding)). An outermost layer may be an exterior coating. An exterior coating may comprise a polymer, such as an opaque polymer.

In some embodiments, a non-waveguide cladding (e.g., a first intermediate cladding, a second intermediate cladding, or an outer cladding) may be a photonic crystal layer having a photonic bandgap (e.g., may be a holey layer in a fiber). For example, a photonic crystal layer may be a two-dimensional photonic crystal.

In some embodiments, a system comprises an optical fiber and a rotary junction, wherein the optical fiber is in optical communication with the rotary junction. For example, an optical fiber may be physically connected to a rotary junction. A system may comprise a probe. A probe may be in optical communication with, and optionally physically connected to, a rotary junction. A rotary junction may be operable to allow rotation of a probe during use.

In some embodiments, a system comprises an optical fiber, a first light source, and a second light source, wherein the first light source is in optical communication with a first waveguide of the fiber and the second light source is in optical communication with a second waveguide of the fiber. In some embodiments, a system comprises an imaging module (e.g., for OCT imaging) and a spectroscopy module (e.g., for near-infrared spectroscopy), wherein the imaging module comprises a first light source and the spectroscopy module comprises a second light source (e.g., different from the first light source). In some embodiments, a system is a catheter (e.g., a cardiac catheter).

Figure 1:
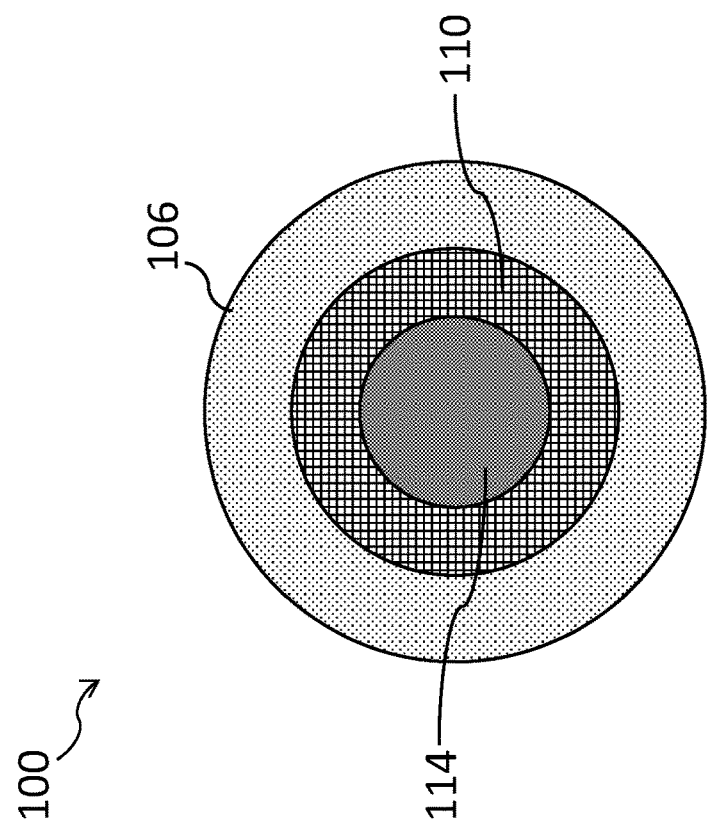
FIG. 1 shows a cross-section of an example of an optical fiber with an attenuating cladding, a waveguide cladding, and a core, according to illustrative embodiments of the disclosure.

FIG. 1 is a schematic of an example of an optical fiber 100. The optical fiber 100 comprises a second waveguide 106, an attenuating cladding 110, and a first waveguide 114. The second waveguide 106 is disposed around the attenuating cladding 110, which is disposed around the first waveguide 114. The second waveguide 106 is a waveguide cladding. The first waveguide 114 is a solid core. The second waveguide 106 is in direct contact with the attenuating cladding 110, which is in direct contact with the first waveguide 114. The first waveguide 114, the attenuating cladding 110, and the second waveguide 106 are concentrically arranged.

FIG. 2 is a schematic of an example of an optical fiber 200. The optical fiber 200 comprises a second waveguide 206, an attenuating cladding 210, and a first waveguide 214. The second waveguide 206 is disposed around the attenuating cladding 210, which is disposed around the first waveguide 214. The second waveguide 206 is a waveguide cladding. The first waveguide 214 is a waveguide cladding. The second waveguide 206 is in direct contact with the attenuating cladding 210, which is in direct contact with the first waveguide 214. In some embodiments, the space 218 shown inside of the first waveguide 214 may be filled by a solid cladding. In some embodiments, the space 218 is filled with gas, such as air.

Figure 3:
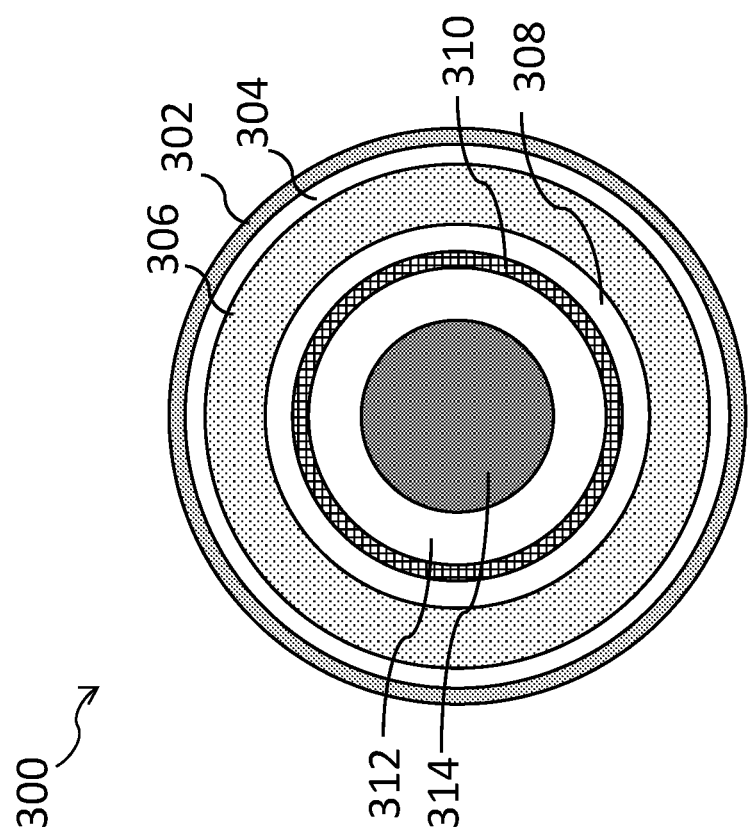
FIG. 3 shows a cross-section of an example of an optical fiber with an attenuating cladding and intermediate claddings, according to illustrative embodiments of the disclosure.

FIG. 3 is a schematic of an example of an optical fiber 300. The optical fiber 300 comprises an outer coating 302, an outer cladding 304, a second waveguide 306, a second intermediate cladding 308, an attenuating cladding 310, a first intermediate cladding 312, and a first waveguide 214. The outer coating 302 is disposed around the outer cladding 304, which is disposed around the second waveguide 306, which is disposed around the second intermediate cladding 308, which is disposed around the attenuating cladding 310, which is disposed around the first intermediate cladding 312, which is disposed around the first waveguide 314. In this example, the second waveguide 306 is disposed around the attenuating cladding 310 and the attenuating cladding 310 is disposed around the first waveguide 314. The outer coating 302 is in direct contact with the outer cladding 304 is in direct contact with the second waveguide 306 is in direct contact with the second intermediate cladding 308 is in direct contact with the attenuating cladding 310 is in direct contact with the first intermediate cladding 312 is in direct contact with the first waveguide 314. The second waveguide 306 is a waveguide cladding. The first waveguide 314 is a solid core. The first intermediate cladding 312 and/or the second intermediate cladding 308 may be a photonic crystal layer having a photonic bandgap (e.g., a two-dimensional photonic crystal).

Figure 4:
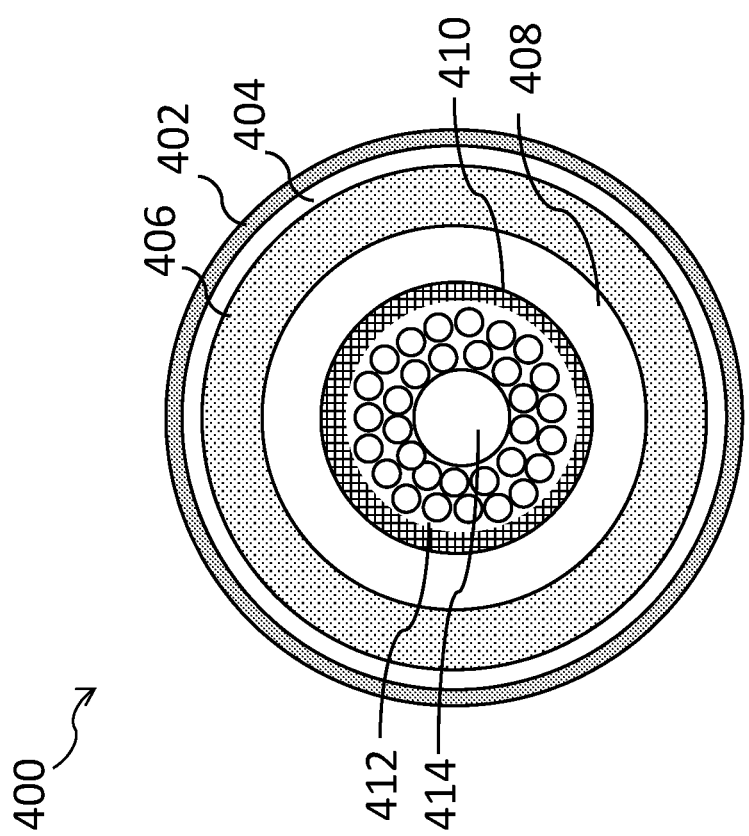
FIG. 4 shows a cross-section of an example of an optical fiber with a hollow core and an attenuating cladding disposed around the hollow core, according to illustrative embodiments of the disclosure.

FIG. 4 is a schematic of an example of an optical fiber 400. The optical fiber 400 comprises an outer coating 402, an outer cladding 404, a second waveguide 406, a second intermediate cladding 408, an attenuating cladding 410, a first intermediate cladding 412, and a first waveguide 414. The outer coating 402 is disposed around the outer cladding 404, which is disposed around the second waveguide 406, which is disposed around the second intermediate cladding 408, which is disposed around the attenuating cladding 410, which is disposed around the first intermediate cladding 412, which is disposed around the first waveguide 414. In this example, the second waveguide 406 is disposed around the attenuating cladding 410 and the attenuating cladding 410 is disposed around the first waveguide 414. The outer coating 402 is in direct contact with the outer cladding 404 is in direct contact with the second waveguide 406 is in direct contact with the second intermediate cladding 408 is in direct contact with the attenuating cladding 410 is in direct contact with the first intermediate cladding 412 is in direct contact with the first waveguide 414. The second waveguide 406 is a waveguide cladding. The first waveguide 414 is a hollow core. The first intermediate cladding 412 is a photonic crystal layer having a photonic bandgap (e.g., a two-dimensional photonic crystal).

Figure 5:
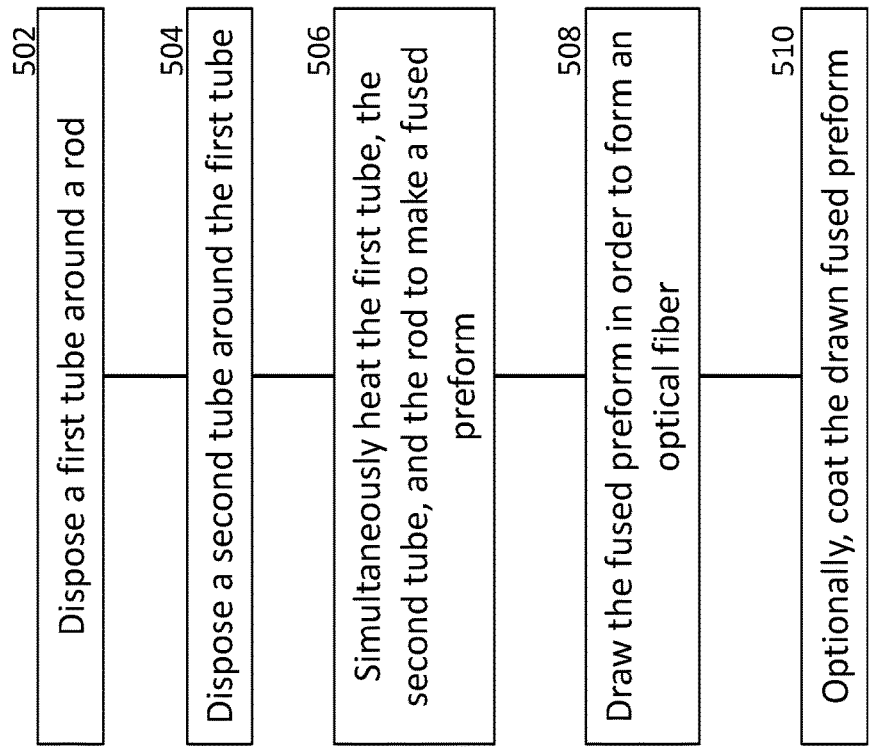
FIG. 5 is a flow diagram of an example of a method for forming an optical fiber with an attenuating cladding, according to illustrative embodiments of the disclosure.

FIG. 5 is a flow diagram of an example of a method 500 for forming an optical fiber. The method 500 is a rod-in-tube type process. The method 500 includes steps 502-508 and optional step 510. In step 502, a first tube comprising attenuating-cladding material is disposed around a rod comprising solid-core material. Solid-core material may be the same or different from waveguide-material. In step 504, a second tub comprising waveguide-cladding material is disposed around the first tube. In step 506, the rod, the first tube, the second tube are simultaneously heated to make a fused preform. In some embodiments, one or more additional tubes (e.g., comprising intermediate-cladding material, waveguide-cladding material, or attenuating-cladding material) are disposed (e.g., between two tubes or between a rod and a two) prior to heating. In step 508, the fused preform is drawn in order to form an optical fiber. For example, a tube heated in step 506 may have an outer diameter of at least 50 mm, at least 100 mm, at least 150 mm, at least 200 mm, at least 300 mm, at least 500 mm, or at least 1 m (e.g., and less than 5 meters), that is drawn in order to form a fiber with substantially smaller diameter (e.g., at least ten times smaller, at least fifty times smaller, at least 100 times smaller, at least 500 times smaller, or at least 1000 times smaller diameter). In optional step 510, the drawn fused preform is coated with an outer coating (e.g., comprising an opaque polymer).

In some embodiments, a method comprises disposing an attenuating tube comprising attenuating-cladding material around a first tube comprising first waveguide material. A second tube comprising second waveguide material may be disposed around the attenuating tube. The first tube, the second tube, and the attenuating tube may be simultaneously heated to make a fused preform. The fused preform may be drawn in order to form an optical fiber. The drawn fused preform may be coated with an outer coating (e.g., comprising an opaque polymer).

Figure 6:
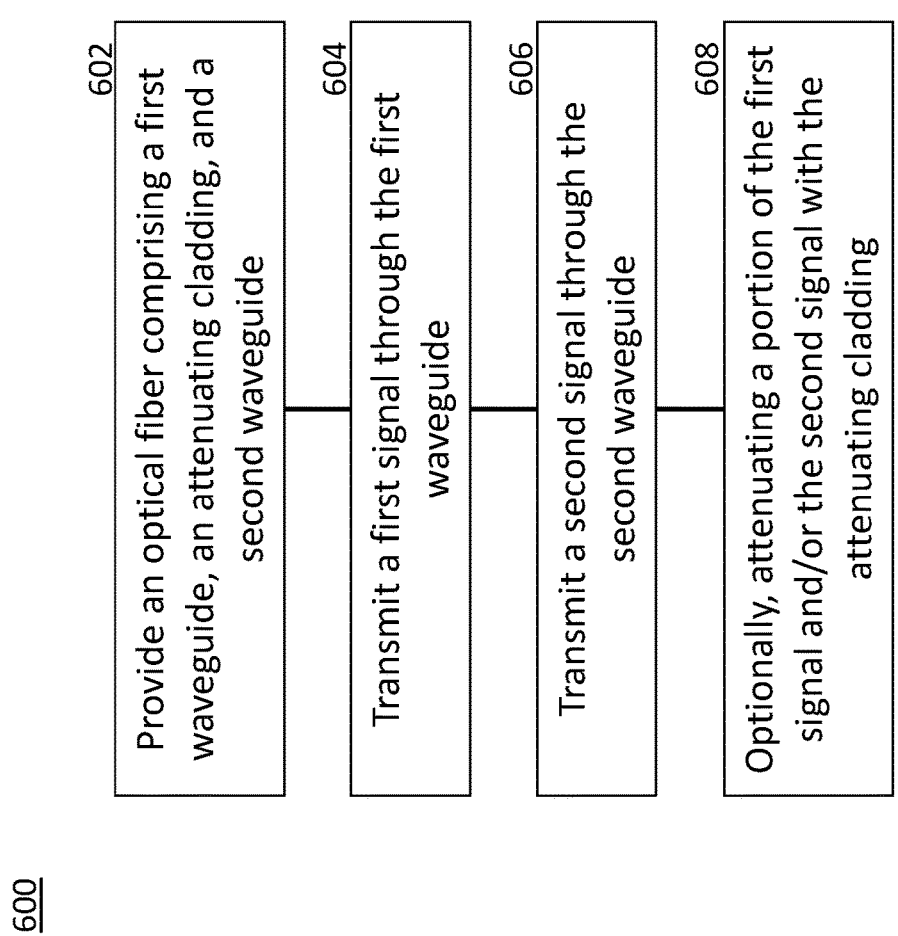
FIG. 6 is a flow diagram of an example of a method for using an optical fiber with an attenuating cladding, according to illustrative embodiments of the disclosure.

FIG. 6 is a flow diagram of an example of a method 600 for using an optical fiber. The method 600 includes steps 602-606 and optional step 608. In step 602, an optical fiber comprising a first waveguide (e.g., a core), an attenuating cladding disposed around the first waveguide, and a second waveguide (e.g., a waveguide cladding) disposed around the attenuating cladding is provided. In step 604, a first signal is transmitted through the first waveguide. In step 606, a second signal is transmitted through the second waveguide. The first signal and the second signal may be transmitted during a same period of time. In optional step 608, a portion of the first signal and/or the second signal is completely attenuated by the attenuating cladding (e.g., thereby preventing it from entering another waveguide or cladding and/or re-entering its originating waveguide). For example, a first portion of the first signal may propagate (e.g., leaks) from the first waveguide into the attenuating cladding and be completely attenuated by the attenuating cladding (e.g., such that the first portion cannot propagate from the attenuating cladding (e.g., into the waveguide cladding or the core)) (e.g., due to absorption of the first portion). For example, a second portion of the second signal may propagate (e.g., leaks) from the second waveguide into the attenuating cladding and be completely attenuated by the attenuating cladding (e.g., such that the second portion cannot propagate from the attenuating cladding (e.g., into the waveguide cladding or the core)) (e.g., due to absorption of the second portion).

Certain embodiments of the present disclosure were expressly described in detail above. It is, however, expressly noted that the present disclosure is not limited to those embodiments, but rather the intention is that additions and modifications to what was expressly described in the present application are also included within the scope of the application. Moreover, it is to be understood that the features of the various embodiments described in the present application were not mutually exclusive and can exist in various combinations and permutations, even if such combinations or permutations were not made express, without departing from the spirit and scope of the application. Having described certain implementations of optical fibers and methods of their formation and their use, it will now become apparent to one of skill in the art that other implementations incorporating the concepts of the application may be used. Therefore, the application should not be limited to certain implementations, but rather should be limited only by the spirit and scope of the following claims.

What is claimed is:

1. A system comprising:
a probe comprising an optical fiber comprising:
    a first waveguide;
    an attenuating cladding disposed around the first waveguide;
    a second waveguide disposed around the attenuating cladding, and
a rotary junction in optical communication with the optical fiber and physically connected to the probe,
wherein the first waveguide and the second waveguide are each constructed, sized, and shaped to transmit light for a sample characterization technique and the attenuating cladding is constructed, sized, and shaped to completely attenuate any of the light that propagates between the first waveguide and the second waveguide into the attenuating cladding.

2. The system of claim 1, wherein the attenuating cladding comprises a dopant, wherein the dopant comprises a metal or boron.

3. The system of claim 2, wherein the attenuating cladding comprises a glass, wherein the dopant is dispersed within the glass.

4. The system of claim 2, wherein the dopant comprises a metallic oxide or a metallic chloride.

5. The system of claim 2, wherein the dopant is a pure metal.

6. The system of claim 1, wherein the attenuating cladding is opaque.

7. The system of claim 1, wherein an attenuation length of the attenuating cladding is no more than 1 meter.

8. The system of claim 7, wherein the attenuation length is between 5 mm and 35 mm.

9. The system of claim 1, wherein the attenuating cladding is constructed, sized, and shaped to attenuate at least 90% of light in a distance of at least 3 mm.

10. The system of claim 9, wherein the attenuating cladding is constructed, sized, and shaped to attenuate at least 90% of light in a distance of between 5 mm and 35 mm.

11. The system of claim 1, wherein an imaginary part of a refractive index of the attenuating cladding is higher than an imaginary part of a refractive index of the first waveguide and an imaginary part of a refractive index of the second waveguide.

12. The system of claim 1, wherein the first waveguide is a solid core.

13. The system of claim 1, wherein the first waveguide is a hollow core.

14. The system of claim 1, wherein the first waveguide, the attenuating cladding, and the second waveguide are disposed concentrically.

15. The system of claim 1, wherein the first waveguide, the attenuating cladding, and the second waveguide each have an outer surface that is circular in in cross section.

16. The system of claim 1, comprising a first intermediate cladding disposed around the first waveguide, wherein the first intermediate cladding is disposed between the first waveguide and the attenuating cladding.

17. The system of claim 16, wherein the attenuating cladding is in direct contact with the first intermediate cladding and the first intermediate cladding is in direct contact with the first waveguide.

18. The system of claim 1, comprising a second intermediate cladding disposed around the attenuating cladding and between the second waveguide and the attenuating cladding.

19. The system of claim 18, wherein the second waveguide is in direct contact with the second intermediate cladding.

20. The system of claim 18, wherein the attenuating cladding has a refractive index that is higher than a refractive index of the first intermediate cladding and a refractive index of the second intermediate cladding.

21. The system of claim 16, wherein the first intermediate cladding, the second intermediate cladding, or both the first intermediate cladding and the second intermediate cladding is a photonic crystal layer having a photonic bandgap.

22. The system of claim 1, wherein the optical fiber is a drawn fiber that has been drawn from a fused preform.

23. A catheter system comprising a system according to claim 1, a first light source, and a second light source, wherein the first light source is in optical communication with the first waveguide and the second light source is in optical communication with the second waveguide.

24. The catheter system of claim 23, comprising an imaging module and a spectroscopy module, wherein the imaging module comprises one of the first light source and the second light source and the spectroscopy module comprises a different one of the first light source and the second light source.

25. A method of using a system, the method comprising:
providing (i) an optical fiber comprising a first waveguide, an attenuating cladding disposed around the first waveguide, and a second waveguide disposed around the attenuating cladding, and (ii) a rotary junction, wherein the optical fiber is in optical communication with the rotary junction;
transmitting a first signal through the rotary junction and through the first waveguide; and
transmitting a second signal through the rotary junction and through the second waveguide,
wherein the first signal is for a first characterization technique and the second signal is for a distinct second technique, and
wherein any signal propagated into the attenuating cladding during the transmitting of the first signal or during the transmitting of the second signal is completely attenuated in the attenuating cladding.

26. The method of claim 25, wherein transmitting the first signal and transmitting the second signal occur simultaneously.

27. The system of claim 1, wherein the first waveguide and the second waveguide are each constructed, sized, and shaped to transmit light for a distinct sample characterization technique.

* * * * *

UNITED STATES PATENT AND TRADEMARK OFFICE
CERTIFICATE OF CORRECTION

PATENT NO. : 11,867,943 B2
APPLICATION NO. : 17/291921
DATED : January 9, 2024
INVENTOR(S) : Martin F. Seifert It is certified that error appears in the above-identified patent and that said Letters Patent is hereby corrected as shown below:

On the Title Page

Left column, under item (73) Assignee:
Replace "Spectra WAVE" with --SpectraWAVE--

Right column, under item (57) Abstract:
Replace "a waveguide (e.g., a waveguide cladding)" with --a second waveguide (e.g., a waveguide cladding)--

In the Claims

Column 15, Claim 15, Line 10:
Delete "circular in in cross section" and replace with --circular in cross section--

Signed and Sealed this
Thirtieth Day of April, 2024

Katherine Kelly Vidal
*Director of the United States Patent and Trademark Office*